United States Patent
Bellinger-Kawahara et al.

(10) Patent No.: US 6,964,856 B2
(45) Date of Patent: Nov. 15, 2005

(54) ANIMAL MODELS AND METHODS FOR SEPSIS

(75) Inventors: Carole Bellinger-Kawahara, Redwood City, CA (US); Pamela R. Contag, San Jose, CA (US); Alan Hubbard, Berkeley, CA (US)

(73) Assignee: Xenogen Corporation, Alameda, CA (US)

( * ) Notice: Subject to any disclaimer, the term of this patent is extended or adjusted under 35 U.S.C. 154(b) by 149 days.

(21) Appl. No.: 10/439,902

(22) Filed: May 15, 2003

(65) Prior Publication Data

US 2003/0203418 A1 Oct. 30, 2003

Related U.S. Application Data

(62) Division of application No. 09/527,061, filed on Mar. 16, 2000, now Pat. No. 6,610,503.
(60) Provisional application No. 60/124,725, filed on Mar. 17, 1999.

(51) Int. Cl.[7] ................................................. C12Q 1/66
(52) U.S. Cl. ............................. 435/8; 424/9.1; 424/9.2
(58) Field of Search ............................. 435/8; 424/9.1, 424/9.2; 800/18

(56) References Cited

U.S. PATENT DOCUMENTS

| | | | |
|---|---|---|---|
| 5,650,135 A | * 7/1997 | Contag et al. | 424/9.1 |
| 6,020,121 A | 2/2000 | Bao et al. | |
| 6,217,847 B1 | 4/2001 | Contag et al. | |
| 6,610,503 B1 | * 8/2003 | Bellinger-Kawahara et al. | 435/8 |

FOREIGN PATENT DOCUMENTS

| | | |
|---|---|---|
| EP | 0 864 648 A1 | 9/1998 |
| WO | WO 96/40979 A1 | 12/1996 |
| WO | WO 97/11690 A2 | 4/1997 |
| WO | WO 97/18841 A1 | 5/1997 |
| WO | WO 97/40381 A1 | 10/1997 |
| WO | WO 00/36106 A2 | 6/2000 |
| WO | WO 01/18195 A2 | 3/2001 |
| WO | WO 01/18225 A1 | 3/2001 |

OTHER PUBLICATIONS

Larrick J. Generation of Protective Human Monoclonal for the Treatment of Gram Negative Sepsis. Progress in Clinical & Biological Research, vol. 272, pp. 383–393, 1988.*
Oka Y. Selective Downregulation of Neutrophils by a Phosphatidic Acid Generation Inhibitor in a Porcine Sepsis Model. J of Surgical Research 81(2)147–155, 1999.*
Contag et al., "Photonic Detection of Bacterial Pathogens in Living Hosts," *Molecular Microbiology* 18(4):593–603 (1995).
Contag et al., "Bioluminescent Indicators in Living Mammals," *Nature Medicine* 4(2):245–247 (1998).
Francis et al., "Monitoring Bioluminescent *Staphylococcus aureus* Infections in Living Mice Using a Novel luxABCDE Construct," *Infection and Immunity* 68(6):3594–3600 (2000).
Louie et al, "Predictive Value of Several Signs of infection as Surrogate Markers for Mortality in a Neutropenic Guinea Pig Model of *Pseudomonas aeruginosa* Sepsis," *Laboratory Animal Science* 47(6):617–623 (1997).

* cited by examiner

Primary Examiner—Ralph Gitomer
(74) Attorney, Agent, or Firm—Robins & Pasternak LLP

(57) ABSTRACT

Methods for selecting a candidate drug for treating sepsis are disclosed. The methods involve labeling a sepsis-causing pathogen with a reporter and monitoring the progress of infection by detecting levels of the reporter in animals treated with test compounds or drugs. The comparisons may be made between experimental and control animals, as well as within a single animal or group of animals. Also disclosed is a method for predicting an expected time of death of an experimental animal in a model system of sepsis using data generated in the initial part of the experiment.

36 Claims, 6 Drawing Sheets

ANIMAL MODELS AND METHODS FOR SEPSIS

CROSS REFERENCE TO RELATED APPLICATIONS

This application is a divisional of U.S. patent application Ser. No. 09/527,061, filed 16 Mar. 2000 now U.S. Pat. No. 6,610,503, issued Aug. 26, 2003, from which priority is claimed under 35 U.S.C. § 120, and which application is related to U.S. Provisional Patent Application Ser. No. 60/124,725 filed Mar. 17, 1999, from which priority is claimed under 35 U.S.C. § 119(e)(1), and which applications are incorporated herein by reference in their entireties.

TECHNICAL FIELD

The present invention relates to animal models of sepsis and methods of use thereof. In particular, the invention relates to methods of predicting survival time of animals with sepsis, and methods of screening test compounds for effectiveness in treating sepsis.

BACKGROUND OF THE INVENTION

Sepsis, or illness caused by a severe infection, is the third leading cause of infectious death (Bone, et al., 1997). The majority of sepsis cases are caused by bacterial infections. Accordingly, a substantial amount of money and time has gone into the search for drugs effective to treat sepsis and/or eliminate the pathogens (e.g., bacteria) which cause sepsis.

Current animal models of sepsis, used primarily to evaluate the efficacy of compounds in treating sepsis, are typically "death as an endpoint" models. In other words, the determination of whether an animal has succumbed to sepsis (or if a particular treatment was effective) is made by scoring whether the animal dies during the course of the experiment.

Such death-as-an-endpoint models have a number of disadvantages. For example, because the investigator must wait until animals die before useful data may be obtained from the study, the study takes longer than it would if such data could be obtained at a time before death of the animals. From an animal welfare standpoint, death-as-an-endpoint models are disadvantageous because the animals die directly from the disease or toxic compounds under study, and are thus more likely to suffer as compared with animals that are euthanized by humane means earlier in the study.

It would therefore be desirable to have a reliable method by which an investigator could accurately predict whether and when a particular animal is likely to die as a result of sepsis without actually waiting for the animal to do so. The present invention provides such a method, as well as related methods suitable for screening drugs effective to treat sepsis

SUMMARY OF THE INVENTION

In one aspect, the invention includes a method for selecting a candidate drug for treating sepsis. The method includes the steps of (i) selecting a model system of sepsis, the model system comprising an animal species and a pathogen species capable of causing sepsis in the animal species, in which model system a critical rate of pathogen load increase has been ascertained; (ii) infecting an experimental animal of the animal species with a dose of reporter-labeled pathogen of the pathogen species, where the dose is sufficient to result in a rate of pathogen load increase exceeding the critical rate; (iii) administering a test drug to the experimental animal; (iv) measuring the level of the reporter in the experimental animal; and (v) selecting the test drug as a candidate drug for treating sepsis if the test drug is effective to decrease the rate of pathogen load increase in the experimental animal below the critical rate of pathogen load increase.

In one embodiment, the pathogen species is a bacterium species and the pathogen is a bacterium, e.g., a bacterium species selected from the group consisting of *Enterococcus* spp., *Staphylococcus* spp., *Streptococcus* spp., Enterobacteriacae family, *Providencia* spp. and *Pseudomonas* spp. An exemplary bacterium is a *Pseudomonas* spp.

In another embodiment, the animal species is a mammal, e.g., a rodent such as a mouse. In yet another embodiment, the reporter is light-emitting reporter, such as a luminescent reporter, e.g., a luciferase enzyme. In still another embodiment, the measuring is done using a photon detection device, such as an intensified CCD camera or a cooled CCD camera.

In another aspect, the invention includes a method for selecting a candidate drug for treating sepsis. The method includes the steps of (i) selecting a model system of sepsis, the model system comprising an animal species and a pathogen species capable of causing sepsis in the animal species, in which animal species (a) a time of onset of terminal sepsis in response to a selected dose of the pathogen species, and (b) a critical infection level of the pathogen species, have been ascertained; (ii) infecting an experimental animal of the animal species with a dose of reporter-labeled pathogen of the pathogen species, where the dose is sufficient to cause the onset of terminal sepsis in an untreated animal; (iii) administering a test drug to the experimental animal; (iv) measuring the level of the reporter in the experimental animal at a selected time after onset of terminal sepsis, where the level of reporter corresponds to the level of infection in the experimental animal; and (v) selecting the test drug as a candidate drug for treating sepsis if the test drug is effective to drop the level of infection below the critical infection level.

In one embodiment, the pathogen species is a bacterium species and the pathogen is a bacterium, e.g., a bacterium species selected from the group consisting of *Enterococcus* spp., *Staphylococcus* spp., *Streptococcus* spp., Enterobacteriacae family, *Providencia* spp. and *Pseudomonas* spp. An exemplary bacterium is a *Pseudomonas* spp.

In another embodiment, the animal species is a mammal, e.g., a rodent such as a mouse. In yet another embodiment, the reporter is light-emitting reporter, such as a luminescent reporter, e.g., a luciferase enzyme. In still another embodiment, the measuring is done using a photon detection device, such as an intensified CCD camera or a cooled CCD camera.

In another aspect, the invention includes a method for selecting a candidate drug for treating sepsis. The method includes the steps of: (i) selecting a model system of sepsis, the model system comprising an animal species and a pathogen species capable of causing sepsis in the animal species, in which animal species a time of onset of terminal sepsis, in response to a selected dose of the pathogen species, has been ascertained; (ii) infecting experimental and control animals of the animal species with a reporter-labeled pathogen of the pathogen species; (iii) administering a test drug to the experimental animals; (iv) measuring the level of reporter in the experimental and the control animals at a selected time after onset of terminal sepsis; and (v) selecting the test drug as a candidate drug for treating sepsis if the test drug is effective to cause a statistically-significant reduction in the level of reporter in the experimental animals as compared with the control animals.

In one embodiment, the pathogen species is a bacterium species and the pathogen is a bacterium, e.g., a bacterium species selected from the group consisting of *Enterococcus* spp., *Staphylococcus* spp., *Streptococcus* spp., Enterobacteriacae family, *Providencia* spp. and *Pseudomonas* spp. An exemplary bacterium is a *Pseudomonas* spp.

In another embodiment, the animal species is a mammal, e.g., a rodent such as a mouse. In yet another embodiment, the reporter is light-emitting reporter, such as a luminescent reporter, e.g., a luciferase enzyme. In still another embodiment, the measuring is done using a photon detection device, such as an intensified CCD camera or a cooled CCD camera.

The invention further includes a method for predicting an expected time of death of an experimental animal in a model system of sepsis. The method includes the steps of:

(i) selecting a model system of sepsis, the model system comprising an animal species and a pathogen species capable of causing sepsis, in which animal species a death expectation curve at a selected time has been constructed,
(ii) infecting an experimental animal of the animal species with a reporter-labeled pathogen of the pathogen species;
(iii) measuring the level of the reporter in the experimental animal at the selected time, and (iv) predicting the expected time of death from the level of the reporter and the death expectation curve.

In one embodiment, the pathogen species is a bacterium species and the pathogen is a bacterium, e.g., a bacterium species selected from the group consisting of *Enterococcus* spp., *Staphylococcus* spp., *Streptococcus* spp., Enterobacteriacae family, *Providencia* spp. and *Pseudomonas* spp. An exemplary bacterium is a *Pseudomonas* spp.

In another embodiment, the animal species is a mammal, e.g., a rodent such as a mouse. In yet another embodiment, the reporter is light-emitting reporter, such as a luminescent reporter, e.g., a luciferase enzyme. In still another embodiment; the measuring is done using a photon detection device, such as an intensified CCD camera or a cooled CCD camera.

The experiment also includes a method of predicting an expected time of death of an experimental animal in a model system of sepsis. The method includes the steps of (i) selecting a model system of sepsis, which model system comprises an animal species and a pathogen species capable of causing sepsis, and in which model system a correlation between actual time of death and a function of the rate of pathogen load increase has been established; (ii) infecting an experimental animal of the animal species with a reporter-labeled pathogen of the pathogen species; (iii) measuring the level of the reporter in the experimental animal at the selected time; and (iv) predicting the expected time of death from the level of the reporter and the correlation.

In one embodiment, the pathogen species is a bacterium species and the pathogen is a bacterium, e.g., a bacterium species selected from the group consisting of *Enterococcus* spp., *Staphylococcus* spp., *Streptococcus* spp., Enterobacteriacae family, *Providencia* spp. and *Pseudomonas* spp. An exemplary bacterium is a *Pseudomonas* spp.

In another embodiment, the animal species is a mammal, e.g., a rodent such as a mouse. In yet another embodiment, the reporter is light-emitting reporter, such as a luminescent reporter, e.g., a luciferase enzyme. In still another embodiment, the measuring is done using a photon detection device, such as an intensified CCD camera or a cooled CCD camera.

Various features of the different embodiments described above may be combined by one of skill in the art in view of the disclosure herein. These and other objects and features of the invention will become more fully apparent when the following detailed description is read in conjunction with the accompanying drawings.

BRIEF DESCRIPTION OF THE FIGURES

FIG. 2A shows the luminescent signal seen immediately after intraperitoneal injection of $1 \times 10^6$ bacteria (t=0). FIG. 2B shows an image taken at t=4.5 hours; FIG. 2C shows an image taken at t=7 hours; and FIG. 2D shows an image taken at t=18 hours (image time=2 min).

DETAILED DESCRIPTION OF THE INVENTION

Figure 1:
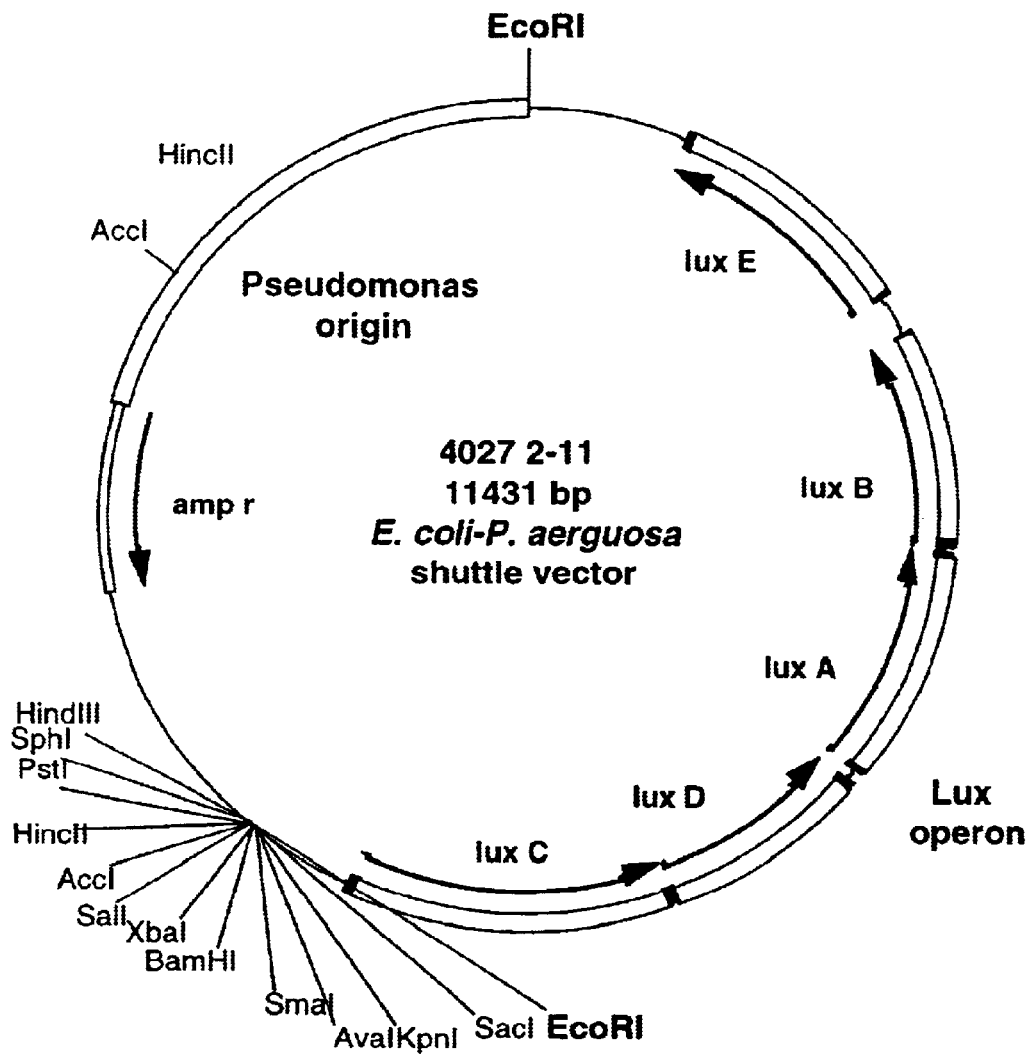
FIG. 1 is a map of *E. coli-P. aeruginosa* shuttle vector 4027 2–11.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); and *Handbook of Experimental Immunology,* Vols. I–IV (D. M. Weir and C. C. Blackwell, eds., 1986, Blackwell Scientific Publications); Ausubel, F. M., et al., *Current Protocols in Molecular Biology,* John Wiley and Sons, Inc., Media Pa.; and Sambrook, et al., *Molecular Cloning: A Laboratory Manual* (2nd Edition, 1989).

As used in this specification and the appended claims, the singular forms "a," "an" and "the" include plural references unless the content clearly dictates otherwise. Thus, for example, reference to "an antigen" includes a mixture of two or more such agents.

1. Definitions

In describing the present invention, the following terms will be employed, and are intended to be defined as indicated below. Unless otherwise indicated, all terms used herein have the same meaning as they would to one skilled in the art of the present invention.

"Animal" as used herein refers to a non-human mammal, including, without limitation, laboratory animals such as rodents (e.g., mice, rats, hamsters, gerbils and guinea pigs); farm animals such as cattle, sheep, pigs, goats and horses; domestic mammals such as dogs and cats; birds, including domestic, wild and game birds such as chickens, turkeys and other gallinaceous birds, ducks, geese, and the like. The term does not denote a particular age. Thus, both adult and newborn individuals are intended to be covered.

"Test compound", "test drug" or "candidate drug" as used herein refer to any compound or substance whose efficacy can be evaluated using the test animals and methods of the present invention. Such compounds or drugs include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds can be employed in the practice of the present invention.

"Sepsis" as used herein refers to a disease or illness caused by a severe infection of the host animal with a pathogen, such as bacteria or a eukaryotic parasite.

"Bacterial sepsis" as used herein refers to sepsis in a host animal caused by a bacterial infection of the host animal.

An "animal model of sepsis" as used herein refers to a species of host animal used in a model of sepsis, without regard to the particular pathogen causing sepsis in that host animal. For example, a mouse model of sepsis would include a mouse model where sepsis is caused by, e.g., *P. aeruginosa*, as well as a mouse model where sepsis is caused by, e.g., *Escherichia coli*.

A "model system of sepsis" as used herein refers to an animal model for sepsis caused by a specific organism. A model system of sepsis is therefore specific to both the host animal and the particular sepsis-causing pathogen under study. For example, one model system of sepsis is a mouse model using *Pseudomonas aeruginosa*, as detailed below in Examples 1–2. A different model system of sepsis is a mouse model using *Enterococcus faecalis*.

An "untreated animal" or "control animal" as used herein refers to an animal that has not been subject to a treatment (e.g., exposure to a test drug) which might affect the progress of bacterial sepsis in the animal.

2. Modes of Carrying Out the Invention

Before describing the present invention in detail, it is to be understood that this invention is not limited to particular formulations or process parameters, as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1 Models of Sepsis

The present invention may be applied in connection with any animal model of sepsis which utilizes the progress of infection by the sepsis-causing pathogen as a basis for the model. Exemplary animal models of sepsis include rodent, rabbit and monkey models. Rodent models are particularly suitable, as they can be carried out economically without need for specialized primate centers. Suitable rodents include mice, rats, hamsters, gerbils and guinea pigs.

For use in connection with the invention, the animal model of sepsis is adapted for use with a particular sepsis-causing organism, such as a eukaryotic parasite or a bacterium. As is recognized in the art, a number of different types of bacteria are capable of causing sepsis. They include, but are not limited to, the following species: Gram positive organisms, such as members of *Enterococcus* spp. (e.g., *E. faecalis*), *Staphylococcus* spp. (e.g., *S. aureus*), and *Streptococcus* spp. (e.g., *S. agalactiae*); and Gram negative organisms, such as members of the Enterobacteriacae family (e.g., *Escherichia coli*), *Providencia* spp. and *Pseudomonas* spp. (e.g., *P. aeruginosa*)

In practicing the present invention, the pathogen causing sepsis is labeled with a reporter, preferably a reporter that can be detected in a living animal. Exemplary reporters with such properties include light-emitting reporters, such as fluorescent and luminescent reporters. A further desirable characteristic of the reporter is that it does not become diluted as the labeled pathogen reproduces. Accordingly, preferred reporters suitable for use with the present invention comprise polypeptides expressed by the pathogen. Polynucleotide cassettes encoding such polypeptides are typically transfected into the pathogen as extra-chromosomal genetic elements (e.g., plasmids) or are stably incorporated into the pathogen genome (e.g., "hopped" in using a transposon).

Polypeptides which result in the generation of light in a living organism (bioluminescence) include, but are not limited to, various luciferases, green fluorescent protein (GFP), yellow fluorescent protein and aequorin (Wilson and Hastings, 1998, *Annu. Rev. Cell Dev. Biol.* 14:197–230). Luciferase is a particularly suitable reporter, since it is a luminescent molecule, and thus does not require excitation in order to generate light. It does, however, typically require a substrate (e.g., luciferin, an aldehyde or coelenterazine), an energy source (e.g., ATP) and oxygen. In the case of bacterial luciferases, the genes encoding the substrate can be supplied the same vector as the gene(s) encoding the luciferase enzyme, thus eliminating the need for exogenously-supplied substrate (see, e.g., U.S. Pat. No. 5,650,135).

In a preferred embodiment of the present invention, the pathogen is transfected with a vector encoding a light-generating protein in order to label the pathogen. Vectors suitable for such transformation are known in the art, and include the vector described in U.S. Pat. No. 5,650,135, as well as the *E. coli-P. aeruginosa* shuttle vector 4027 2–11 described in the Materials and Methods, below. Of course, other transformation methods, plasmids, vectors, or methods of integrating polynucleotides into the genome, known in the art, may be used by one of skill in the art to label a selected sepsis-causing pathogen with a selected polypeptide-based reporter.

After the pathogen is labeled with a suitable reporter, it is introduced into a selected animal model of sepsis for use with the present invention. If the reporter is a light-generating reporter, it may be imaged within the living host animal as described, e.g., in U.S. Pat. No. 5,650,135, and related publications (e.g., Contag, et al., 1998, *Nature Medicine* 4(2):245–247; and Contag, et al., 1995, *Molecular Microbiology* 18(4):593–603).

It is desirable to calibrate the experimental system to ascertain variables and parameters useful in adapting the methods of the invention to different model systems of sepsis. This process is illustrated for the model system comprising a mouse *Pseudomonas aeruginosa* model of sepsis in the section titled "Calibration Process". In those cases where the parameters determined in the calibration process (e.g., $LD_{50}$, the critical rate of pathogen load increase, time of onset of terminal sepsis, critical infection level and/or death expectation curve) are already known (e.g., from previous experiments or publications), the calibration process may, of course, be bypassed and the invention practiced (e.g., methods for screening drugs; methods for prediction of time of death based on a reporter signal at a selected time) using the known parameters.

One of the factors typically determined in the calibration process is a suitable dose of pathogen for the selected model system of sepsis. This dose is preferably based on the $LD_{50}$ of the pathogen in the particular animal model of sepsis being used. The $LD_{50}$, or "Lethal Dose 50", is a measure for quantifying the effects of a perturbation (e.g., a test compound, procedure, or bacterial infection) on a biological system. It represents the 50% mortality point—that is, the concentration or level of a particular perturbation at which half of the animals die by the end of the experiment.

The $LD_{50}$ may change depending on the experimental parameters. The measure is therefore expressed as an $LD_{50}$ for a given experimental system. By way of example, it was discovered in the course of experiments performed in support of the present invention that the type of anesthesia used to prepare the animals for imaging can have a significant effect on the $LD_{50}$. Specifically, it was discovered that anesthesia induced by injectable Ketamine may potentiate the virulence of some pathogens. In one set of experiments, luminescent *Pseudomonas aeruginosa* had an $LD_{50}$ of approximately $2.5 \times 10^6$ CFU in non-anesthetized mice versus $4.6 \times 10^5$ CFU in Ketamine-sedated mice.

No surprisingly, the $LD_{50}$ is also affected by treatment with compounds which affect the host immune system. For example, it was found during experiments performed in support of the present invention that pathogen virulence is boosted by administration of 5% (by volume) hog gastric mucin to the host. This common adjuvant impairs local macrophage function for 2–3 hours after administration (Comber, et al., 1975, *Antimicrob. Agents Chemother.* 7:179–185).

Although different experimental manipulations, such as types of anesthesia or the presence of mucin, may alter the initial input dose needed to establish terminal sepsis, they do not impact the predictive nature of the methods herein, so long as the calibrations (described below) are carried out under experimental conditions similar to those used in subsequent screening studies.

The $LD_{50}$ is a reliable measure of the ultimate effect of a particular perturbation, but is a very crude readout of the state of the biological system (e.g., animal) since it reduces an underlying graded response in the animal to an all or nothing event (the survival or death of the animal). The $LD_{50}$ provides no information about the state of the animals before they die (e.g., the progress of an infection by the pathogen under study) or after they die (e.g., identification of the underlying pathology, such as identification of specific organ system(s) which failed).

As will be appreciated in view of the following sections, the present invention provides a read-out of the processes underlying a sepsis infection in any given model system of sepsis, and provides methods by which this read-out can be quantitatively related to the traditional $LD_{50}$ in that model system. In this way, it provides a method for studying the progress of sepsis in living animals, and for predicting the time of death for a particular animal, so the effects of a particular compound or treatment can be assessed the without waiting for the animal to die.

2.2 Calibration Process

A. Overview of Exemplified Calibration Process

Examples 1 through 5, below, illustrate an approach which may be used according to the present invention to generate calibration data for a model system of sepsis (a mouse—*P. aeruginosa* model). A similar approach may be taken to obtain such calibration data for other model systems of sepsis, e.g., a mouse with other types of bacteria, as well as other experimental animals (e.g., gerbils, rats, etc.) infected with different types of pathogens (microbes, parasites, etc).

Two independent calibration processes are described. The first (illustrated in Examples 1–3) involves assessing adjustment and trend periods, the onset of terminal sepsis, the construction of a death expectation curve, and/or the determination of a critical infection level. The second (illustrated in Examples 4 and 5) involves the determination of a critical rate of pathogen load increase. Both processes share certain features in common, including the preparation of a pathogen innoculum for injection, the determination of a suitable dose of pathogen, the optional immunosuppression of the host animal, and the administration of the pathogen to the host animal.

B. General Principles

Preparation of Pathogen Inoculum for Injection A pathogen inoculum suitable for infecting a host animal in an animal model of sepsis may be prepared according to standard methods known in the art. For example, a bacterial inoculum may be prepared in general as follows (a specific application is described in the Materials and Methods): Bacteria are grown to early log phase in an appropriate culture medium (with or without antibiotic selection) and are harvested. Harvesting may, for example, be by centrifugation, e.g., at 6000×g for 10 minutes. Following harvesting, the bacteria are typically resuspended in sterile buffer and maintained on ice (at 4° C.), The concentration of the bacteria is estimated, e.g., by measuring absorbance at 600 nm, and is adjusted to a concentration such that the total dose administered to the animal is in a volume suitable for the selected route of administration. For example, in a mouse model where the selected route of administration is intraperitoneal (i.p.) injection, the maximum volume is typically about 0.25 ml or less.

The actual dosage injected is typically confirmed by plating dilutions of the inoculum, growing up the plates, and counting colonies.

Determination of a suitable dose of pathogen Doses of the administered sepsis-causing pathogen (e.g., bacteria) are preferably selected so that most of the animals receive a dose that is within the range defined by about an order of magnitude below to about two orders of magnitude above the $LD_{50}$ for that particular model system of sepsis (i.e., for a particular pathogen/host animal combination).

Immunosuppression of the Experimental Animals Methods of the invention do not require the use of immunosuppressed experimental or host animals, but the invention may be practiced, if desired, using such immunosuppressed animals. The primary difference between normal and immunosuppressed animals is the $LD_{50}$ of the sepsis-causing pathogen, which is substantially lower in immunosuppressed animals. A suitable method for immunosuppression is presented in the Materials and Methods section. The experiments detailed in the Examples were conducted with normal (i.e., non-immunosuppressed) animals.

Administration of Pathogen to the Experimental Animal The pathogen inoculum may be administered to a selected experimental animal following any suitable route of administration, including but not limited to intraperitoneal, intravenous, intramuscular, and intraarterial. In an exemplary approach, bacteria are administered intraperitoneally, as detailed in Example 1, below.

Application of Standard Statistical Methods

It will be understood that standard statistical procedures may be used to place confidence limits on any predictive features of the methods described herein. Such procedures are known in the art (see, e.g., Reed and Muench, 1938, *The American Journal of Hygiene* 27(3):493–497; F. James Rohlf, F. J. and R. R. Sokal, 1994, "Biometry The Principles and Practice of Statistics in Biological Research", $3^{rd}$ ed., W H Freeman & Co), and may be applied by the skilled artisan to, e.g., construct a death expectation curve or death time correlation that will predict, with known confidence limits, the likelihood that an animal having a certain reporter signal at a selected time will die within a specific time interval.

C. Calibration Method 1—Adjustment and Trend Periods, Terminal Sepsis, Death Expectation Curves, and Critical Infection Level Adjustment and Trend Periods It has been discovered, in the course of experiments performed in support of the present invention (described in Example 2, below), that initial infection of a host animal by a sepsis-causing bacterium is typically characterized by an early fluctuation in the numbers of bacteria (termed "adjustment period"), followed by the establishment of a trend in the signal from each animal over time (termed "trend period"). During the adjustment period, the levels of bacteria (as detected by signal from the reporter, e.g., a luminescent reporter) may not necessarily correlate with either the initial bacterial load administered to the animals, or with the ultimate fate of the infected host animal.

During the trend period, however, the level of reporter detected from the animal is roughly proportional to the dose of bacteria initially administered. In other words, the level of reporter is lowest in animals that received a low, sub-$LD_{50}$ dose, intermediate in animals that received a dose comparable to the $LD_{50}$, and highest in animals that received a dose greater than the $LD_{50}$. This relationship is exemplified in the data shown in FIG. 3. At the 24 hour timepoint, the lowest signal, or reporter level, was obtained from mice infected with $10^5$ organisms, an intermediate signal level was obtained from mice infected with $5 \times 10^5$ organisms, and the highest levels were obtained from bacteria infected with $10^6$ organisms.

Onset of Terminal Sepsis The "breakpoint" between the adjustment period and the trend period is defined as the "onset of terminal sepsis". Note that a true breakpoint, or onset of terminal sepsis, occurs only in those animals that succumb to the infection and eventually die. Those animals that clear the infection (e.g., because of a low initial dose or successful treatment) do not exhibit an onset of terminal sepsis. When the invention is practiced with more than one animal per experiment (i.e., a group or groups of animals), and a method step relates a point in time to the onset of terminal sepsis, that point in time for that experiment will be understood to be at the onset of terminal sepsis for the animal that received the lowest dose of pathogen and still developed terminal sepsis, i.e., died of the infection.

Figure 3:
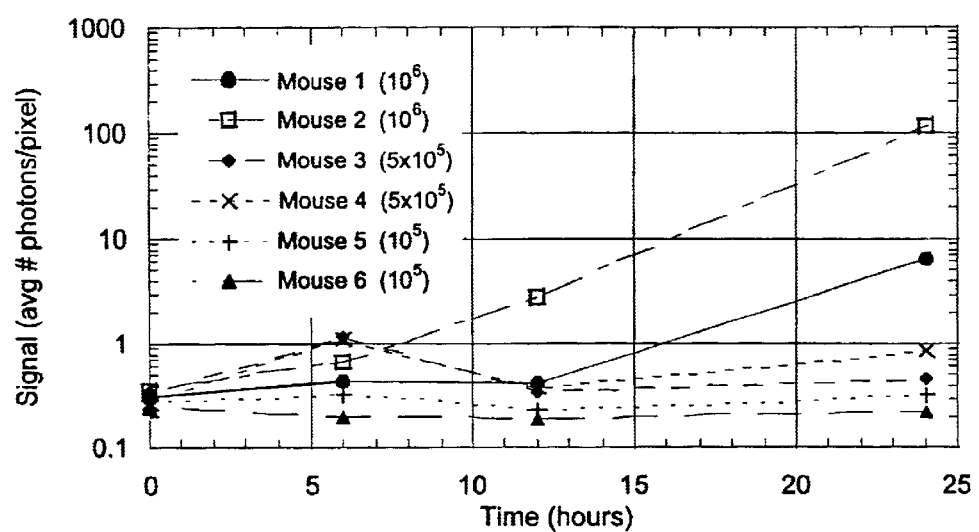
FIG. 3 is a plot of the progression of signal intensity over time from 6 animals infected with doses ranging from $1 \times 10^5$ to $1 \times 10^6$ bacteria.

This is illustrated for the data shown in FIG. 3. Here, the onset of terminal sepsis was established between 12 and 24 hours for all animals that would eventually succumb to sepsis, except for Mouse 2, where it was established between 6 and 12 hours. Using the above approach, the "onset of terminal sepsis" for the entire experiment would thus be between 12 and 24 hours.

To complete the calibration process, the animals are preferably monitored & imaged at suitable intervals until all the animals have either died or have cleared the infection.

Figure 4A:
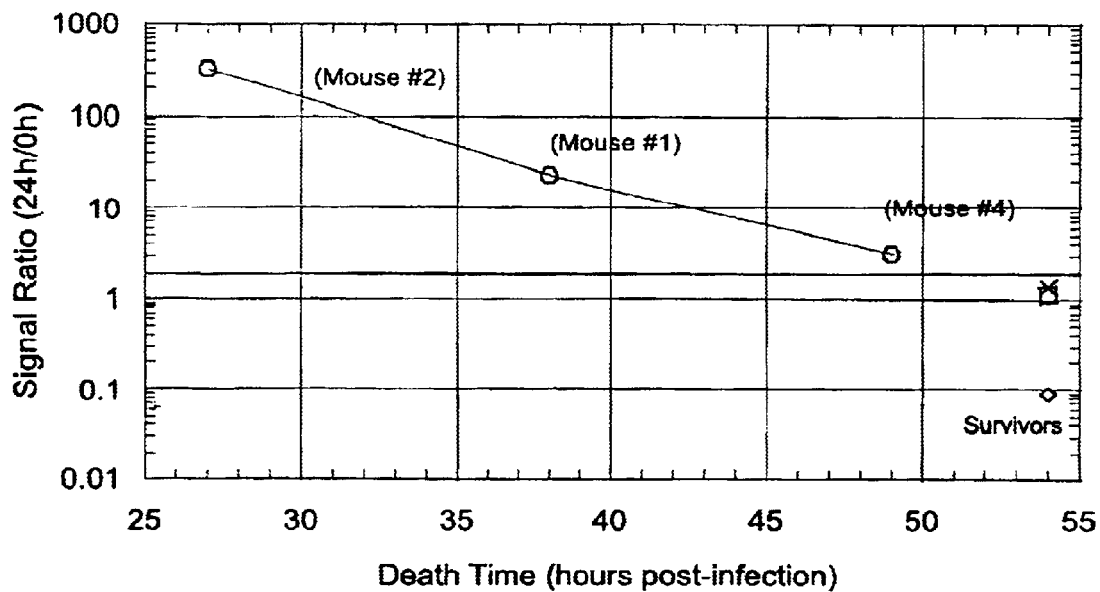
FIG. 4A is a "death expectation curve" constructed using a ratio of the signal at t=24 h to the signal at t=0 h for the mouse/*P. aeruginosa* model system of sepsis.
Figure 4B:
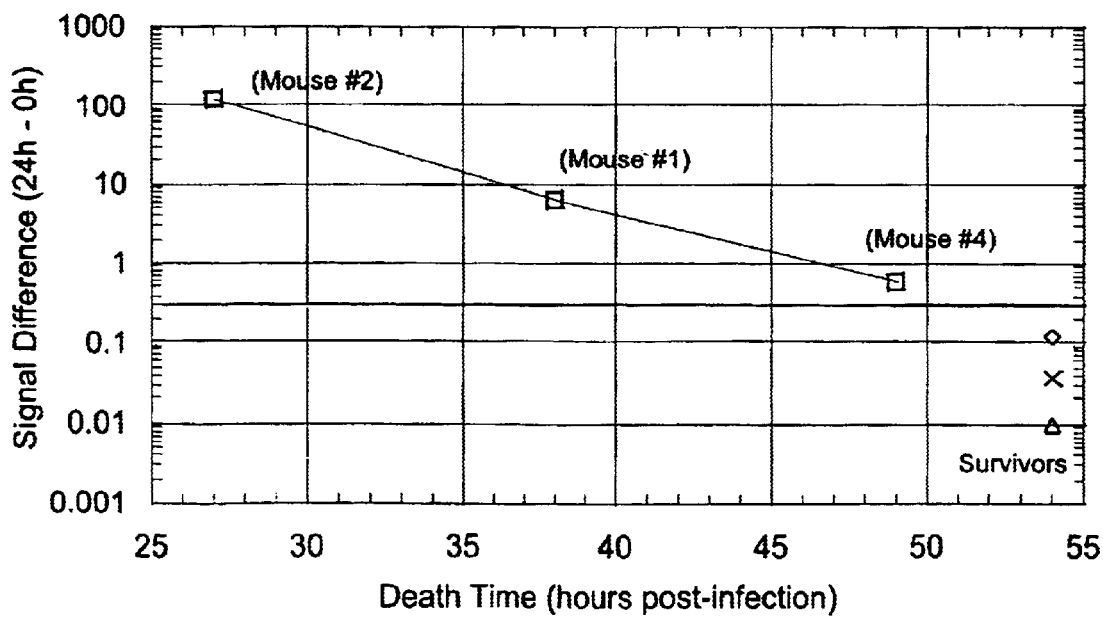
FIG. 4B is a "death expectation curve" constructed using the difference between the signal at t=24 h and the signal at t=0 h for the mouse/*P. aeruginosa* model system of sepsis.

Constructing a death expectation curve Following a determination of the onset of terminal sepsis for a particular calibration experiment, a death expectation curve is constructed. Each mouse in the calibration process is represented by a single point on the death expectation curve. The data in the curve are a measure of the increase of the luminescence signal at a convenient time after onset of terminal sepsis plotted against the time of death of the mouse. Examples of such death expectation curves are shown in FIGS. 4A and 4B for the data described in Example 3. Here, death expectation curves were constructed with data measured 24 hours after the initial inoculation. It will be understood, however, that any convenient time may be used, so long as it is after the onset of terminal sepsis. As mentioned above, the death expectation curve should be constructed at a time after the trend period has started for terminal animals having received the lowest doses of bacteria.

There are several different measures for the increase in the luminescence signal at the selected measurement time. For example, one may use the magnitude of the signal (in photons or photons per unit area) at the time the curve is measured (the "critical time"); a ratio of the signal at the critical time to the signal at time zero; or a difference in the signal at the critical time relative to the signal at time zero.

According to the present invention, the death expectation curve can be used to predict whether a particular animal will clear the sepsis infection or die, and if the prognosis is death, when the death will occur. The animal is simply imaged at the selected measurement time, and the appropriate measure of luminescence is plotted to determine expected time of death.

Determining a Critical Infection Level The death expectation curve will have no data points below a certain signal level, termed "critical infection level". This level is indicated by a solid line in FIGS. 4A and 4B. The critical infection level is useful in predicting whether a particular sepsis treatment will be effective, since lowering the bacterial signal below the critical infection level is indicative of an effective candidate drug for treating bacterial sepsis.

D. Calibration Method 2—Determining the Critical Rate of Pathogen Load Increase

Figure 5A:
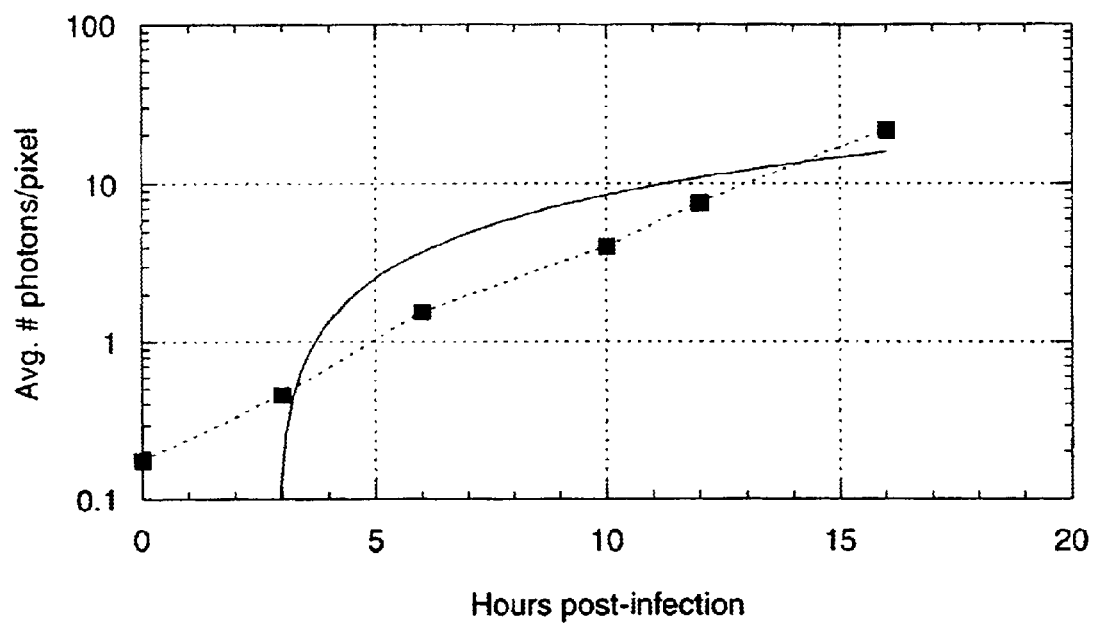
FIGS. 5A and 5B show luminesce intensity obtained at indicated times after infection in mouse 39d5×10e5m5 (FIG. 5A) and mouse 39d5×10e5m6 (FIG. 5B). The data are superimposed with a linear fits (solid lines).
Figure 5B:
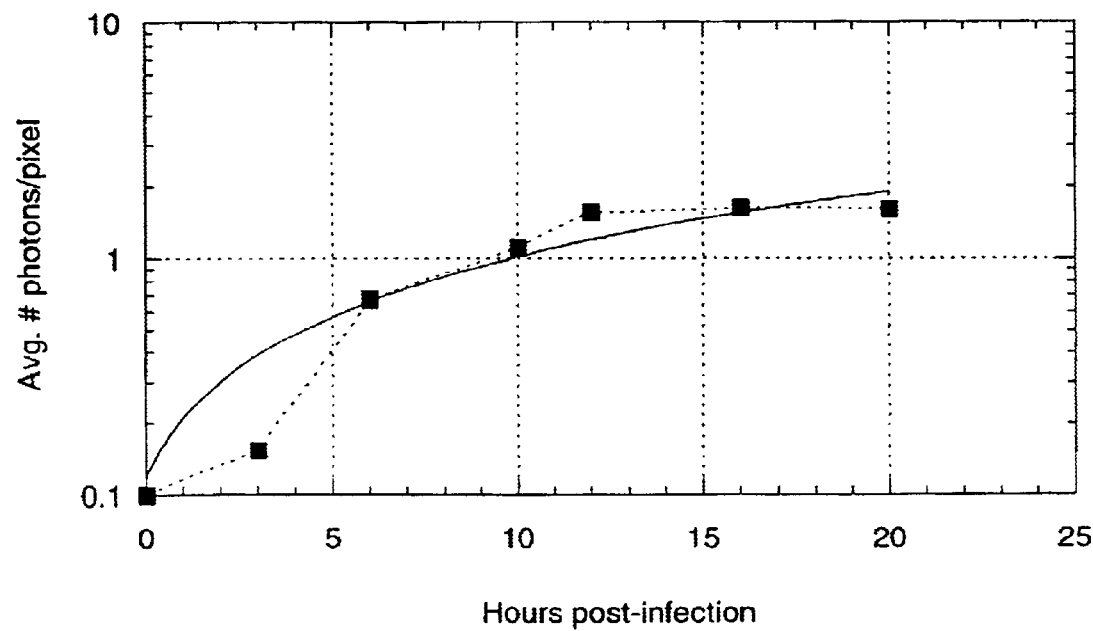
Figure 6:
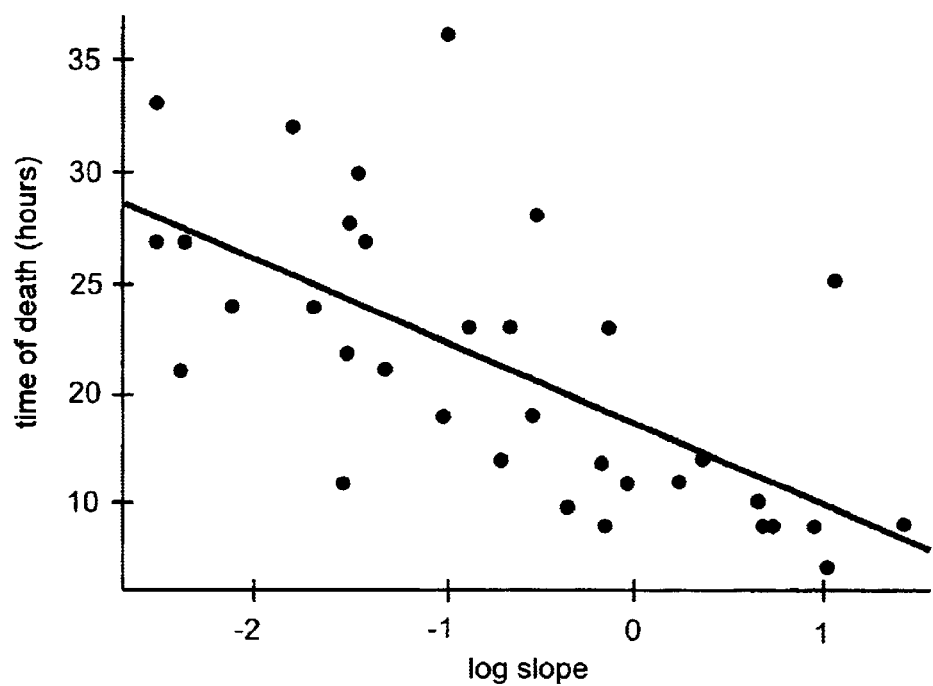
FIG. 6 is a graph plotting log slope and time of death (in hours). The data are superimposed with a linear fit (solid line).

According to a preferred embodiment of the present invention, an estimate of whether an animal with sepsis is likely to live or die after a specific period of time (e.g., 60 hours) can be reliably obtained by determining the critical rate of pathogen load increase, as detailed in Example 5. Specifically, the host animals are inoculated with a selected light-producing bacterium as described above, with doses selected to fall in the same order of magnitude as the range of $LD_{50}$ values. The luminescent signal in each mouse is imaged in vivo at a series of selected intervals and quantified as relative number of photons per pixel (an arbitrary unit of light intensity which does not necessarily correspond to the actual number of photons per pixel). The data are then plotted (e.g., on a semi-log scale) and fitted with a least squares linear curve fitting routine, e.g., as described in Examples 4 and 5. Exemplary data are shown in FIGS. 5A & 5B, and Table 3.

The data are then used to obtain a calibration data set for predicting which animals would likely survive and which would likely die in that particular model system of sepsis. The slopes from linear fits to data collected during an initial portion (e.g., the first 15 hours) of the experiment are analyzed with respect to survival status i.e., whether a particular animal lives or dies, as described in Example 5.

The period of time over which data needs to be acquired in order to form a meaningful calibration data set, and to obtain from the set a critical rate of pathogen load increase, depends primarily on the particular model system of sepsis under study, and to some extent on the number of animals used to generate the data set and the frequency of measurements. In general, using longer measurement times results in a higher degree of confidence in any resulting critical rate of pathogen load increase. The drawback of longer measurement times is that they extend the duration of experiments and may be less effective at alleviating animal suffering due to sepsis.

For example, if a calibration measurement is made and there is significant overlap in slopes from survivors and slopes from animals that died, the slope should calculated over a longer time period to decrease such overlap.

In general, as described in Example 5, it is possible to define a slope which best discriminates among data from deaths on the one hand, and survivors on the other. This slope is termed the "critical rate of pathogen load increase".

2.3 Applications

General Considerations

The methods followed in the following applications are similar to those carried out during the calibration process. Typically, a model system of sepsis is calibrated using the same procedure as will be used during the subsequent application. For example, in cases where the investigator wishes to use the "rate of pathogen load increase" method, both the calibration and the subsequent application (e.g., drug screening) will employ a calculation of the rate of pathogen load increase in the data analysis. Similarly, if the investigator wishes to use adjustment and trend periods, terminal sepsis, death expectation curves, and/or critical infection level parameters in the calibration, data from subsequent applications (e.g., drug screening) will be analyzed in the context of the same parameters.

Selection of Candidate Drugs for Treating Sepsis

The invention described herein may be applied in a number of ways readily apparent to one of skill in the art. For example, the invention includes methods for selecting a candidate drug for treating sepsis. In the methods, a suitable model system of sepsis is selected. Selecting such a model system includes selecting the host animal for the model, as well as a pathogen capable of causing sepsis in that host animal. Examples of suitable animals and sepsis-causing pathogens are provided above. Preferred animal species include mammals, especially rodents such as rats, hamsters, gerbils and guinea pigs. Examples of applicable pathogens include bacteria, such as *Enterococcus* spp., *Staphylococcus* spp., *Streptococcus* spp., Enterobacteriacae family, *Providencia* spp. and *Pseudomonas* spp. It will be understood that the preceding host animals and pathogens are merely illustrative—a variety of sepsis models and sepsis-causing pathogens are known in the art, and may be used in connection with the practice of the present invention.

Once a model system is selected, parameters such as the critical rate of pathogen load increase, or a time of onset of terminal sepsis in response to a selected dose of the pathogen and a critical infection level of the pathogen, are typically ascertained. The parameters may be ascertained in several ways, e.g., by using a calibration process such as is described above, or from previously-performed calibration experiments or published data.

In one method of selecting a candidate drug, an experimental animal is infected with a dose of reporter-labeled pathogen of the appropriate pathogen species, where the dose is sufficient to cause the onset of terminal sepsis in an untreated animal. The pathogen (e.g., bacterium) is preferably labeled with a light-emitting reporter, such as a luminescent reporter, e.g., a luciferase enzyme. A test drug is then administered to the host or experimental animal. The drug may be administered at any suitable time, e.g., before infection, or at a selected time after infection, depending on what type of effect is being screened for (prophylactic or therapeutic).

The level of the reporter is then measured, preferably at a selected time after onset of terminal sepsis (or after the time by which an untreated animal would exhibit onset of terminal sepsis with the particular dose of pathogen administered). If the reporter is a light-emitting reporter, a preferred method of measurement is using a photon detection device, such as an intensified CCD camera, a cooled CCD camera, or any other photon detection device with a high sensitivity. However, other methods may of course be used. For example, a light-emitting reporter may also be detected using a sensitive luminometer; a radioactive reporter may be detected by counts, X-ray imaging or scintillation. Since the reporter labels the pathogen, the level of reporter corresponds to the level of infection by the pathogen of the experimental or host animal.

A test drug which is effective to reduce the level of reporter is then selected as a suitable candidate drug for treating sepsis. If the model system of sepsis is calibrated using the rate of pathogen load increase method, the suitable drug for treating sepsis reduces the rate of pathogen load increase relative to untreated animals exposed to the same dose of pathogen. In a preferred embodiment, the suitable drug for treating sepsis reduces the rate of pathogen load increase below the critical rate of pathogen load increase, under conditions where most of the untreated animals exhibit a rate of pathogen load increase greater than the critical rate. Alternatively, if the model system of sepsis is calibrated in the context of a critical infection level, the suitable drug for treating sepsis preferably reduces the level of reporter detected below the critical infection level.

Candidate drugs for treating sepsis may be evaluated further. Examples of such further evaluation may include additional studies (e.g., different drug dosages, times of administration, different pathogen dosages, etc.) in the present model system of sepsis, as well as other studies, such as toxicology studies, pharmacology studies, and clinical trials. Candidate drugs which prove effective in such follow-up studies may then be commercially produced for treatment of sepsis according to standard production methods known in the art. In this respect, the invention includes methods of screening for such candidate drugs which further include the subsequent manufacture or sale of the candidate drug for treatment of sepsis.

Another method which may be used to select a candidate drug for treating sepsis employs groups of control and experimental animals. The method is performed as described above, except that the pathogen, e.g., bacterium, is used to infect both experimental and control animals with the reporter-labeled pathogen. The test drug is then administered only to the experimental animals, and reporter levels in the experimental animals are compared to reporter levels in controls by any of the preceding methods. Of course, the test drug may be administered according to any suitable dosage or administration protocol, prophylactically or therapeutically.

In one embodiment, the level of reporter in the experimental and the control animals is measured at a selected time after onset of terminal sepsis. A candidate drug may be identified by looking for a statistically-significant reduction in the level of reporter in the experimental animals as compared with the control animals.

In another embodiment, a series of measurement are made over the time interval used for generating a critical rate of pathogen load increase. A candidate drug may be identified by looking for a statistically-significant reduction in the rate of pathogen load increase in the experimental animals as compared with the control animals.

Predicting an Expected Time of Death of a Host Animal Using a Death Expectation Curve Another application of the present invention involves a method for predicting an expected time of death of an experimental animal in a model system of sepsis. A model system of sepsis is selected as described above. A death expectation curve is then constructed at a selected time after onset of terminal sepsis for all doses administered in the experiment. The death expectation may be constructed using any of the methods previously mentioned herein. An experimental animal is then infected with a reporter-labeled pathogen of the appropriate pathogen species, and the level of reporter is measured at about the same time after infection as the data used to construct the death expectation curve. The level of reporter is then used to predict the expected time of death using the death expectation curve.

It can be appreciated that this method provides a sensitive measure of the state of the animal during the course of the sepsis-causing infection (which a death-as-an-endpoint model does not), as well as a measure of expected time of death, which can be compared and/or correlated with data generated using traditional death-as-an-endpoint $LD_{50}$ studies.

Predicting Survivors Using the Critical Rate

According to one embodiment of the present invention, an estimate of whether an animal with sepsis is likely to live or die after a particular period of time (e.g., 60 days) can be obtained by determining the critical rate of pathogen load increase as detailed in Examples 4 and 5. The critical rate can then be used, e.g., during subsequent drug screens in the same model system of sepsis, to predict the expected effectiveness of a potential treatment for sepsis, without carrying the experiment to lethal endpoints.

The following examples illustrate but in no way are intended to limit the present invention.

MATERIALS AND METHODS

Unless otherwise indicated, chemicals were purchased from Sigma (St. Louis, Mo.) or United States Biochemical (Cleveland, Ohio). The abbreviation "mcg" refers to "micrograms".

A. Buffers

Phosphate-Buffered Saline (PBS), pH 7.4

8000 mg/l NaCl 200 mg/l KCl 1150 mg/l $Na_2HPO_4$ 200 mg/l $KH_2PO_4$

B. Construction of E. coli-P. aeruginosa shuttle vector 4027 2–11

E. coli-P. aeruginosa shuttle vector 4027 2–11 was constructed as follows: The Pseudomonas aeruginosa origin of replication was cut from plasmid pRO1600 (Jansons, I., et al., 1994, Plasmid 31:265–74) with StuI and blunt ended. The blunt-ended fragment was then cloned into a blunted NdeI site in plasmid pGEM-3zf(+)(Promega Corporation, Madison, Wis.) to produce plasmid 4027. The lux operon from the soil bacterium Xenorhabdus luminescens (Frackman, et al., 1990, J. Bact. 172:5767–5773) was cut from plasmid pCGLS1 (Meighen, E. A. and Szittner, R. B., 1992, J. Bacteriol. 174:5371–5381) with EcoRI and cloned into the EcoRI site of 4027 to produce vector 4027 2–11. A map of vector 4027 2–11 is shown in FIG. 1.

C. Construction of Luminescent Pseudomonas aeruginosa

Pseudomonas aeruginosa cells were transformed with shuttle vector 4027 2–11 using calcium chloride transformation. Briefly, P. aeruginosa competent cells were made using the method of Hanahan, D., 1983 (J. Mol. Biol. 166:557–580) and transformed with vector 4027 2–11 using the method of Cambau, E., et al., 1995 (Antimicrobial Agents and Chemotherapy 39:2248–2252). The resulting light-emitting strain was designated 2–11 lux.

D. Immunosuppression of Mice

Mice are immunosuppressed by two injections of cyclophosphamide: one at four days before the experiment (day −4), and another the day before the experiment (day −1). On day −4, each mouse receives one i.p. dose of cyclophosphamide (stock solution at 5 mg/ml in PBS) calculated at 150 mg/kg body weight. The second dose on day −1 is given i.p. at 100 mg/kg.

E. Anesthesia

Mice were anesthetized with a 4:1 (v/v) mixture of ketamine (100 mg/ml in PBS) and xylazine (20 mg/ml in PBS), mixed immediately prior to injection with bacteria. The anesthetic mixture was injected intramuscularly in the left thigh at a dose of 100 mg ketamine/kg body weight.

F. Imaging

Animals were imaged essentially as described in U.S. Pat. No. 5,650,135. Luminescence was quantified using a either an intensified photon-counting camera (Hamamatsu Photonics Model 2400–32) or a cooled integrating camera (e.g., a Princeton Instruments Model LN/CCD 1340–1300-EB/1 or a Roper model LN-1300-EB). All of the above cameras use a charge-coupled device array (CCD array) to generate a signal proportional to the number of photons per selected unit area. The selected unit area may be as small as that detected by a single CCD pixel, or, if binning is used, that detected by any selected group of pixels. This signal may optionally be routed through an image processor, such as the Argus available from Hamamatsu Photonics, and then transmitted to a computer (either a PC running Windows NT (Dell Computer Corporation; Microsoft Corporation, Redmond, Wash.) or a Macintosh (Apple Computer, Cupertino, Calif.) running an image-processing software application, such as "LivingImage" (Xenogen Corporation, Alameda, Calif.). The software and/or image processor are used to acquire an image, stored as a computer data file. The data generally take the form of (x, y, z) values, where x and y represent the spatial coordinates of the point or area from which the signal was collected, and z represents the amount of signal at that point or area, expressed as the relative number of photons per pixel (photons/pixel). It will be understood that this an arbitrary measure presented for the purpose of comparing different data sets, and does not necessarily reflect the absolute number of photons per pixel.

To facilitate interpretation, the data are typically displayed as a "pseudocolor" image, where a color spectrum is used to denote the z value (amount of signal) at a particular point. Further, the pseudocolor signal image is typically superimposed over a reflected light or "photographic" image to for an "overlay" image, which provides a frame of reference for the luminescence data. Unless otherwise indicated, luminescence data were collected for 5 minutes for each image.

Luminescence values used to generate the "Avg. # photons/pixel" data used in Exampled 2–6, below, were measured as follows. A overlay image was acquired from the ventral side of the animal as described above. The animals were always measured at the same distance from the camera lens, and at the same magnification, so that meaningful comparisons could be made using data from different animals. The overlay image to be analyzed was displayed on a computer monitor using the software "LIVINGIMAGE" (Xenogen Corp., Alameda, Calif.). A oval measuring-tool was superimposed on the image and adjusted in size (maintaining its aspect ratio) such that the width of the oval corresponded to the width of the animal in the overlay image. The aspect ratio of the oval was such that the head and limbs of the animal were generally excluded from the oval. The total luminescence signal within the oval was then summed and divided by the number of pixels represented within the oval, thereby yielding one number (expressed as the "Avg. # photons/pixel") for each overlay animal image. This number was then used in calculating the various measures of pathogen load, infection level, etc., that are described below.

G. Preparation of Bacteria for IP Injection

Cultures of luminescent *Pseudomonas aeruginosa* 2–11 lux were grown overnight (18–24 hr, 37° C., shaking at 180–200 rpm) in Luria-Bertani broth containing 100 mcg/ml carbenicillin. Two ml of an overnight culture were diluted into 20 ml of fresh growth medium and grown at 37° C., shaking at 180–200 rpm for 90–120 minutes in order to reach early to mid log phase. Bacteria were then harvested by centrifugation at 6000 ×g for 10 minutes at 0° C.

The pelleted bacteria were resuspended in 2.0 ml PBS buffer, and the absorbance of a 1:100 dilution of the suspension was measured at 600 nm ($A_{600}$) to estimate the number of viable bacteria, using the following conversion: 0.45 $A_{600}$=~5×10$^8$ colony-forming units/ml. The bacterial concentration of the original suspension was then adjusted to the desired experimental dosages by dilution into PBS buffer.

EXAMPLE 1

Development of Septicemia

Figure 2D:
FIGS. 2A–2D are images of the development of bacterial sepsis in mice, as measured by light output of luminescent *Pseudomonas aeruginosa* over 24 hours.
Figure 2C:
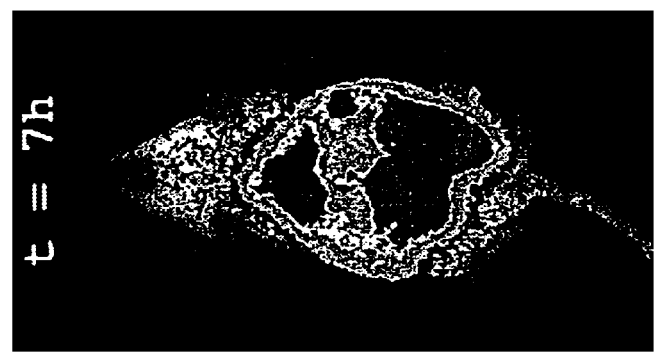
Figure 2B:
Figure 2A:
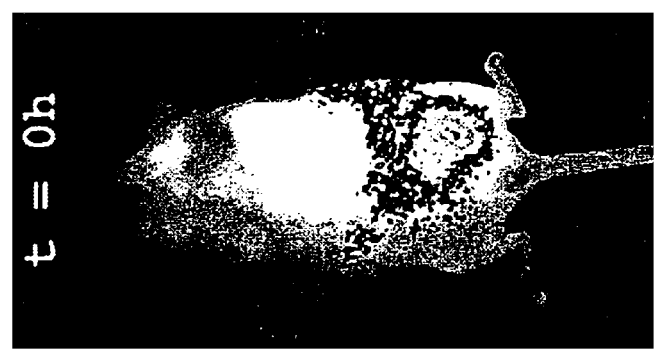

Female Balb/c mice (10–12 weeks old), anesthetized as described above, were injected intraperitoneally (i.p.) with 1×10$^6$ luminescent 2–11 lux *P. aeruginosa* bacteria suspended in a total volume of 0.25 ml, and imaged at selected times as described above. Exemplary images are shown in FIGS. 2A, 2B, 2C and 2D. FIGS. 2A, 2B and 2C are images from one of the mice, taken at t=0, 4.5 and 7 hours, respectively. FIG. 2D is an image of another (similarly-infected) mouse taken at 18 hours. The relative intensity of photon counts is shown in pseudocolor in both images, and is superimposed over a grayscale reflected light image of the mouse in FIGS. 2A, 2B and 2C.

EXAMPLE 2

Signal Increase with Time in Mice Infected with 2–11 lux

Six female Balb/c mice (8–12 weeks old), anesthetized as described above, were injected i.p. with 2–11 lux *P. aeruginosa* as described above. The doses were selected to fall in the same order of magnitude as the range of $LD_{50}$ values from previous studies with this species. Mice 1 and 2 received 1×10$^6$ bacteria, mice 3 and 4 received 5×10$^5$ bacteria, and mice 5 and 6 received 1×10$^5$ bacteria. The luminescent signal in each mouse was imaged in vivo at 0, 6, 12, and 24 hours post-infection and quantified as relative number of photons per pixel. The data are summarized in Table 1, below, and graphed in FIG. 3.

TABLE 1

| Time (h) | Mouse 1 | Mouse 2 | Mouse 3 | Mouse 4 | Mouse 5 | Mouse 6 |
|---|---|---|---|---|---|---|
| 0 | 0.309 | 0.362 | 0.349 | 0.271 | 0.282 | 0.238 |
| 6 | 0.446 | 0.693 | 1.170 | 1.130 | 0.328 | 0.198 |
| 12 | 0.418 | 2.810 | 0.335 | 0.374 | 0.233 | 0.185 |
| 24 | 6.380 | 118.60 | 0.464 | 0.866 | 0.319 | 0.220 |

FIG. 3 shows the signal, in average number of photons per pixel, for the 6 mice, at 6, 12 and 24 hours. It can be appreciated from the data that there is an initial (at 6 hour timepoint) fluctuation in signal levels (the adjustment period), followed by the establishment of a trend in the signal from each animal over time (the trend period). During the trend period, the signal values are correlated with the initial dose of bacteria as described above.

EXAMPLE 3

Death Expectation Curve

The mice described in Example 2 were monitored for 55 hours. Mice 1, 2, and 4 died during the course of the experiment, whereas mice 3, 5, and 6 were able to clear the infection. Based on the data in FIG. 3 and Table 1, above, the onset of terminal sepsis for this experiment was determined to be between 12 and 24 hours post-infection. The 24 hour time point was selected as a convenient point in time after the onset of terminal sepsis, but before the death of the animals, for use in constructing death expectation curves. The curves were thus constructed based on the survival information and the signal data at 24 hours, which are summarized below in Table 2.

TABLE 2

| Mouse # | Dose | Signal 0 hours | Signal 24 hours | Delta | Ratio | Time of Death |
|---|---|---|---|---|---|---|
| 1 | 1.E+06 | 0.309 | 6.83 | 6.52 | 22.1 | ~38 h |
| 2 | 1.E+06 | 0.362 | 118 | 118 | 327 | ~27 h |
| 3 | 5.E+05 | 0.349 | 0.464 | 0.115 | 1.33 | Survived |
| 4 | 5.E+05 | 0.271 | 0.866 | 0.595 | 3.20 | ~49 h |
| 5 | 1.E+05 | 0.282 | 0.319 | 0.037 | 1.13 | Survived |
| 6 | 1.E+05 | 0.238 | 0.220 | −0.018 | 0.92 | Survived |

Death expectation curves were constructed by plotting a measure of the signal at 24 hours (either the raw signal at t=24 hours, the difference between the signal at t=24 hours and the signal at t=0 hours, or the ratio of the signal at t=24 hours. The measures gave comparable results in terms of predicting the time of death of infected animals.

Death expectation curves constructed using (i) the "difference" or "delta" data, and (ii) the "ratio" data, are shown in FIGS. 4A and 4B, respectively. The data points for survivors are shown for comparison. They are show on the plots at 54 hours, although it will be understood that these animals did not actually die at 54 hours, but survived the experiment. Further, to facilitate display of the data on a log scale, the "delta" or "difference" value for Mouse #6 was set at 0.01 for purposes of FIGS. 4A and 4B.

A critical infection level is shown in both FIGS. 4A and 4B as a solid line below the signal value representing the lowest level of infection which caused death, and above the signal values from surviving mice.

EXAMPLE 4

Signal Increase with Time in Mice Infected with *P. aeruginosa* Xen-5

Fifty nine female Balb/c mice (8–12 weeks old), anesthetized as described above, were injected i.p. with luminescent *P. aeruginosa* as described above. The doses were selected to fall in the same order of magnitude as the range of $LD_{50}$ values from previous studies with this species, and ranged between $2 \times 10^4$ and $2 \times 10^6$ bacteria. The luminescent signal in each mouse was imaged in vivo at a series of intervals (typically 0, 3, 6, 10, 12, and 16 hours) post-infection and quantified as the average number of photons per pixel (see "Imaging" under Materials and Methods, above). The data were plotted on a semi-log scale, and were fitted with a linear curve fit using the least squares fitting routine supplied in the software program "KALEIDA-GRAPH" (Synergy Software, Reading, Pa.).

Exemplary data are shown in FIGS. 5A and 5B. The graphs show luminesce intensity (solid squares) and a linear fit to the data (curved line on this semi-log plot). FIG. 5A contains data from mouse 39d5×10e5m5, with linear fit parameters of $y=-3.40+1.19x$ ($R=0.87$), and FIG. 5B contains data from mouse 39d5×10e5m6, with linear fit parameters of $y=0.12+0.09x$ ($R=0.94$).

The 59 animals were followed for 60 hours post infection. The times of death of animals that died during the 60 hour experiment period were noted. For example, mouse 39d5× 10e5m5 died at t=19 hours, while mouse 39d5×10e5m6 died at t=24 hours.

EXAMPLE 5

Prediction of Survival Based on the Critical Rate of Pathogen Load Increase

Data collected from the 59 mice described in Example 4 were assessed to identify data from animals which met certain criteria for inclusion in subsequent analyses. The criteria for determining whether data from a particular animal would be included were (i) at least five good photon images from must have been acquired from the animal during the experiment, and (ii) the animal must have died from sepsis. Death from sepsis was defined as death following a pattern of infection whereby at least 50% of the abdominal area of the animal was luminescent in at least one of the five images acquired during the experiment. The "death from sepsis" distinction was made because infection in a few of the animals that ultimately died remained localized in a small spot during the course of the experiment, suggesting that these animals may not have died from sepsis.

Data from 49 of the original 59 animals met the above criteria and collectively formed a calibration data set which was analyzed and then used for predicting which animals would likely survive and which would likely die in the model system of sepsis detailed in Examples 4 and 5.

The calibration data set was analyzed by correlating the slopes from the linear fits to data collected during the first 15 hours of the experiment (see Example 4, above) with survival status (i.e., whether a particular animal lived or died). The results are shown in Table 3, below.

TABLE 3

| Survivor Status | Slope | | |
|---|---|---|---|
| | Mean | Std. Dev. | Freq |
| Death | 0.98 | 1.0 | 30 |
| Survivor | 0.0043 | 0.021 | 19 |
| Total | 0.60 | 0.93 | 49 |

As can be seen from Table 3, the average slope from animals that died during the 60 hours of experiment (0.98) is substantially greater than the average slope from animals that lived (0.0043). Indeed, data from all of the animals that eventually died had a slope of greater than 0.080, whereas data from all of the animals that remained alive after 60 hours had slopes of less than 0.080.

It can be appreciated that the slope of the fits to the data described above is a measure of the rate of pathogen load increase in the animal during the first 15 hours of the experiment. Animals which had a rate of pathogen load increase of less than 0.080 over the first 15 hours survived, whereas animals that had a rate of pathogen load increase of more than 0.080 died before the end of the 60-hour experiment. The slope of 0.080 was thus termed the "critical rate of pathogen load increase", since it was the rate of pathogen load increase that best discriminated (in this case, perfectly) among data from animals that would die within the 60 hours on the one hand, and animals that would survive the experiment (survivors) on the other.

As noted above, in this particular experiment, the calibration data were such that the critical rate of pathogen load increase (or simply the "critical rate") discriminated perfectly between animals destined to die and those destined to survive. In other words, the slope of fits to data generated during the first 15 hours of the experiment was a perfect predictor of whether an animal would be dead or alive at 60 hours post-infection.

EXAMPLE 6

Prediction of Time of Death using the Rate of Pathogen Load Increase and Survival Statistics A subset of the data analyzed in Example 4, above, was used to construct a plot for predicting an estimated time of death based on the rate of pathogen load increase. The data for this analysis were from animals that met the criterion of Example 5 and that died before the end of the experiment, so the actual time of death could be analyzed. The log of the slope of the fits generated as described in Example 4 was plotted (on the x-axis) against the actual time of death (on the y-axis), and the data were subjected to a regression analysis. A linear fit to the log(slope) fit the data reasonably well, with an estimated standard deviation of the residuals of about 6. The 95% confidence interval of prediction was about 24 hours.

The data demonstrate that it is possible to obtain an estimate of the time of death using data generated during only an initial portion of an experiment.

While the invention has been described with reference to specific methods and embodiments, it is appreciated that various modifications and changes may be made without departing from the invention.

What is claimed is:

1. A method for selecting a candidate drug for treating sepsis, comprising:
   (i) selecting a model system of sepsis, said model system comprising an animal species and a pathogen species that causes sepsis in said animal species, in which model system a critical rate or pathogen load increase has been ascertained, (ii) infecting an experimental animal of said animal species with a dose of reporter-labeled pathogen of said pathogen species, where said dose is sufficient to result in a rate of pathogen load increase exceeding said critical rate;

(iii) administering a test drug to said experimental animal;

(iv) measuring the level of said reporter in said experimental animal; and (v) selecting said test drug as a candidate drug for treating sepsis if said test drug is effective to decrease the rate of pathogen load increase in the experimental animal below said critical rate of pathogen load increase.

2. The method of claim 1, wherein the pathogen species is a bacterium species and the pathogen is a bacterium.

3. The method of claim 2, wherein the bacterium species is selected from the group consisting of *Enterococcus* spp., *Staphylococcus* spp., *Streptococcus* spp., Enterobacteriacae family, *Providencia* spp. and *Pseudomonas* spp.

4. The method of claim 3, wherein the bacterium is a *Pseudomonas* spp.

5. The method of claim 1, wherein the animal species is a mammal.

6. The method of claim 5, wherein the mammal is a rodent.

7. The method of claim 6, wherein the rodent is a mouse.

8. The method of claim 1, wherein the reporter is light-emitting reporter.

9. The method of claim 8, wherein the light-emitting reporter is a luminescent reporter.

10. The method of claim 9, wherein the reporter comprises a luciferase enzyme.

11. The method of claim 8, wherein the measuring is done using a photon detection device.

12. The method of claim 11, wherein the photon detection device is selected from the group consisting of an intensified CCD camera and a cooled CCD camera.

13. A method for selecting a candidate drug for treating sepsis, comprising:

(i) selecting a model system of sepsis, said model system comprising an animal species and a pathogen species capable of causing sepsis in said animal species, in which animal species a time of onset of terminal sepsis, in response to a selected dose of said pathogen species, has been ascertained;

(ii) infecting experimental and control animals of said animal species with a reporter-labeled pathogen of said pathogen species;

(iii) administering a test drug to said experimental animals;

(iv) measuring the level of reporter in said experimental and said control animals at a selected time after onset of terminal sepsis; and (v) selecting said test drug as a candidate drug for treating sepsis if said test drug is effective to cause a statistically significant reduction in the level of reporter in said experimental animals as compared with said control animals.

14. The method of claim 13, wherein the pathogen species is a bacterium species and the pathogen is a bacterium.

15. The method of claim 14, wherein the bacterium species is selected from the group consisting of *Enterococcus* spp., *Staphylococcus* spp., *Streptococcus* spp., Enterobacteriacae family, *Providencia* spp. and *Pseudomonas* spp.

16. The method of claim 15, wherein the bacterium is a *Pseudomonas* species.

17. The method of claim 13, wherein the animal species is a mammal.

18. The method of claim 17, wherein the mammal is a rodent.

19. The method of claim 18, wherein the rodent is a mouse.

20. The method of claim 19, wherein the reporter is light-emitting reporter.

21. The method of claim 20, wherein the light-emitting reporter is a luminescent reporter.

22. The method of claim 21, wherein the reporter comprises a luciferase enzyme.

23. The method of claim 20, wherein the measuring is done using a photon detection device.

24. The method of claim 23 wherein the photon detection device is selected from the group consisting of an intensified CCD camera and a cooled CCD camera.

25. A method for selecting a candidate drug for treating sepsis, comprising:

(i) selecting a model system of sepsis, said model system comprising an animal species and a pathogen species capable of causing sepsis in said animal species, in which animal species (a) a time of onset of terminal sepsis in response to a selected dose of said pathogen species, and (b) a critical infection level of said pathogen species, have been ascertained;

(ii) infecting an experimental animal of said animal species with a dose of reporter-labeled pathogen of said pathogen species, where said dose is sufficient to cause the onset of terminal sepsis in an untreated animal;

(iii) administering a test drug to said experimental animal;

(iv) measuring the level of said reporter in said experimental animal at a selected time after onset of terminal sepsis, where said level of reporter corresponds to the level of infection in said experimental animal; and (v) selecting said test drug as a candidate drug for treating sepsis if said test drug is effective to drop the level of infection below said critical infection level.

26. The method of claim 25, wherein the pathogen species is a bacterium species and the pathogen is a bacterium.

27. The method of claim 26, wherein the bacterium species is selected from the group consisting of *Enterococcus* spp., *Staphylococcus* spp., *Streptococcus* spp., Enterobacteriacae family, *Providencia* spp. and *Pseudomonas* spp.

28. The method of claim 27, wherein the bacterium is a *Pseudomonas* species.

29. The method, of claim 25, wherein the animal species is a mammal.

30. The method of claim 29, wherein the mammal is a rodent.

31. The method of claim 30, wherein the rodent is a mouse.

32. The method of claim 31, wherein the reporter is light-emitting reporter.

33. The method of claim 32, wherein the light-emitting reporter is a luminescent reporter.

34. The method of claim 33, wherein the reporter comprises a luciferase enzyme.

35. The method of claim 32, wherein the measuring is done using a photon detection device.

36. The method of claim 35 wherein the photon detection device is selected from the group consisting of an intensified CCD camera and a cooled CCD camera.

\* \* \* \* \*